United States Patent [19]
Merkus

[11] Patent Number: 6,007,834
[45] Date of Patent: Dec. 28, 1999

[54] NASAL MELATONIN COMPOSITION

[75] Inventor: Franciscus W. H. M. Merkus, Kasterlee, Belgium

[73] Assignee: Merkus, Franciscus W.H.M., Kasterlee, Belgium

[21] Appl. No.: 09/048,465

[22] Filed: Mar. 26, 1998

[30] Foreign Application Priority Data

Mar. 26, 1997 [EP] European Pat. Off. ............... 9720092
Mar. 24, 1998 [EP] European Pat. Off. .. PCT/EP98/01783

[51] Int. Cl.⁶ ....................................................... A61F 13/02
[52] U.S. Cl. ............................................................ 424/434
[58] Field of Search .................................... 424/434, 449

[56] References Cited

U.S. PATENT DOCUMENTS 4,407,481 10/1983 Bolton et al. .
4,819,834 4/1989 Thiel .
5,449,683 9/1995 Wurtman, II ........................... 514/405

FOREIGN PATENT DOCUMENTS 0094157 11/1983 European Pat. Off. .
0463653 1/1992 European Pat. Off. .
0475482 3/1992 European Pat. Off. .
55-057563 4/1980 Japan .

OTHER PUBLICATIONS

Vollrath et al., *Adv. Bioscience*, 29 (1981), pp. 327–329.
Gennaro et al., Remington's Pharmaceutical Sciences, 18th ed., Mack Publishing Company, 1990, see Part 8: Pharmaceutical Prepar and Their Manufacture.
Database WPI, Week 8040, Derwent Publications Ltd., London, GB; AN 80–70195C '40! –XP002036405.

*Primary Examiner*—Carlos A. Azpuru
*Attorney, Agent, or Firm*—Jones, Day, Reavis & Pogue

[57] ABSTRACT

A pharmaceutical composition for intranasal administration, comprising melatonin and a pharmaceutically acceptable excipient, which is effective to cause the blood plasma melatonin concentration in a human adult, receiving an amount of melatonin in the range of 50–1000 μg and in a single or simultaneous intranasal administration of said composition, to reach at least X pg/ml, within 30 minutes of said administration, wherein X is equal to 5 times the amount of melatonin, expressed in μg, in said single or simultaneous administration.

94 Claims, 1 Drawing Sheet

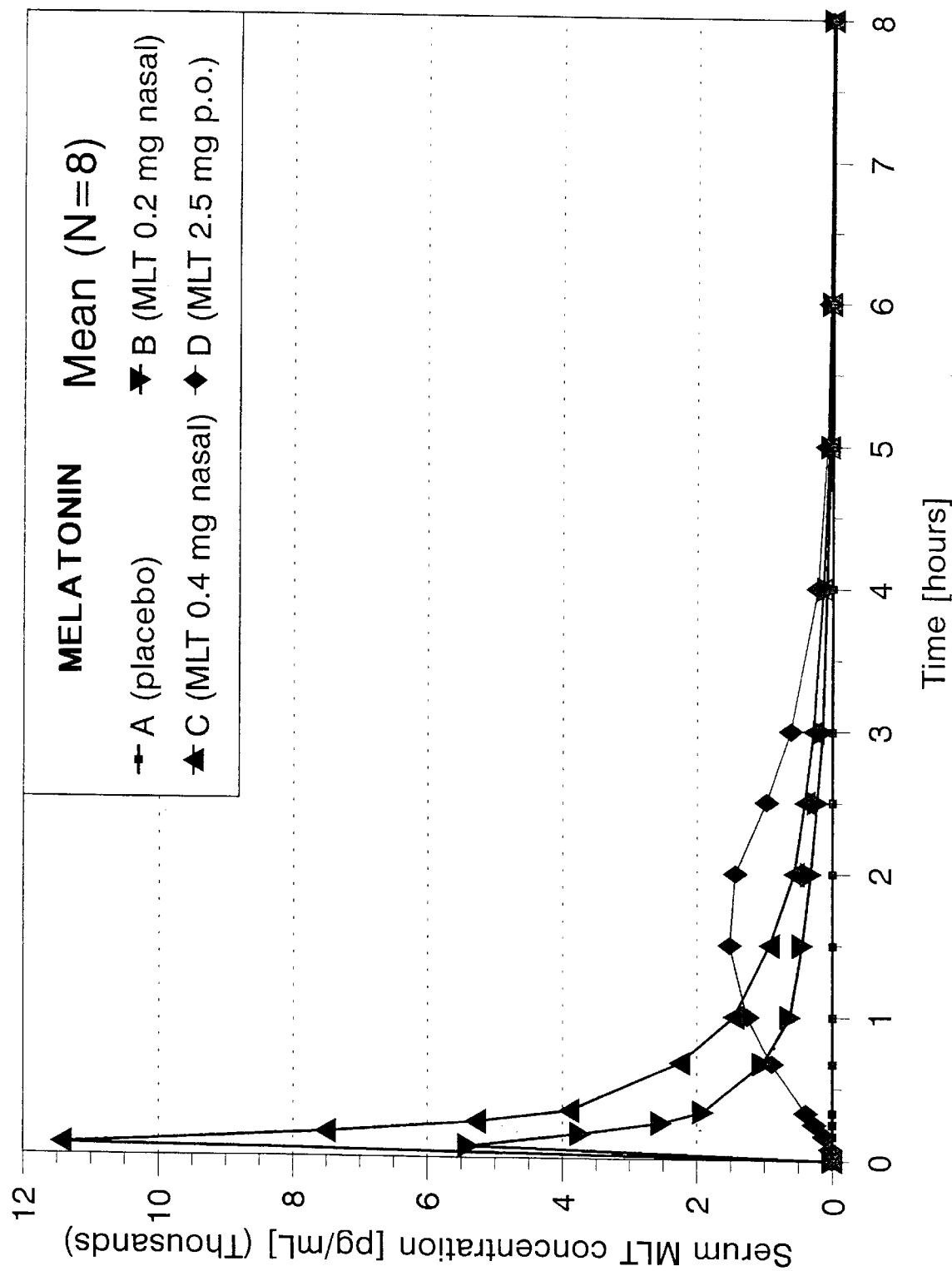

NASAL MELATONIN COMPOSITION

DESCRIPTION

This invention relates to a pharmaceutical composition for intranasal administration of melatonin. The invention further relates to doses or dosage units for intranasal administration, and the use of the same for the preparation of an intranasal dosage form.

Melatonin (N-acetyl-5-methoxytryptamine) is a neurohormone secreted from the pineal gland. It has been disclosed in numerous references that melatonin induces sleep when administered to a patient. The sleep-inducing effects of melatonin have advantages over conventional hypnotics, since not being a hypnotic drug itself, it only induces a state of sleepiness without having the adverse side-effects of conventional hypnotics. Melatonin is usually administered orally but, as with most oral preparations, it takes over an hour after administration for the blood plasma concentration of the active agent (melatonin) to reach its peak. Other routes of administration, in particular nasal administration have been considered. However, because of inherent problems, inter alia due to the low solubility of melatonin in water, melatonin compositions suitable for nasal administration have yet to be prepared.

In an early attempt to develop such a composition, Vollrath et ala, *Adv. Bioscience*, 29 (1981), pp. 327–329 described the nasal administration of 1.7 mg of melatonin in ethanol. Due to serious local irritation and painful administration, this composition was found to be unsuitable for use in man. In 1980, intranasal compositions containing reduced quantities of ethanol were disclosed in Japanese patent application J55057563 (Hoechst AG). A composition of 100 mg of melatonin in 10 ml of a 5% solution of ethanol in water was proposed, but even this still causes an unacceptable degree of adverse side-effects. This patent application also disclosed a composition in which propylene glycol was used in place of ethanol.

Although this second composition would not cause the acute problems associated with ethanol, it is not suitable for nasal use because of the toxicity of propylene glycol, which adversely affects the nasal mucosa.

Therefore, up until the present time, a pharmaceutically acceptable melatonin composition, capable of providing a fast onset time, has yet to be developed.

This problem has now been solved in accordance with the present invention which provides, in a first aspect, a pharmaceutical composition for intranasal administration, comprising melatonin and a pharmaceutically acceptable excipient, characterized by being effective to cause the blood plasma melatonin concentration in a human adult, receiving an amount of melatonin in the range of 50–1000 μg and in a single or simultaneous intranasal administration of said composition, to reach at least X pg/ml within 30 minutes of said administration, wherein X is equal to 5 times the amount of melatonin, expressed in jig, in said single or simultaneous administration.

X is preferably equal to 10, 15, 20 or 25 times the quantity of melatonin, expressed in μg, in said single or simultaneous administration and the amount of melatonin in said administration can be in the range of 100–800 or 200–400 mg. Preferably, a composition in accordance with the invention is effective to cause the blood plasma melatonin concentration in a human adult, receiving 200 μg of melatonin in a single or simultaneous intranasal administration of said composition, to reach at least 1000 pg/ml and, preferably, at least 2000, 3000, 4000, or 5000 pg/ml, within 30 minutes of administration.

In preferred embodiments, said melatonin concentrations are reached within 15, 10, 8, 7, 6 or 5 minutes of administration. Compositions in accordance with this aspect of the invention can also comprise a saccharide, a polysaccharide or a triol.

In further preferred embodiments, compositions in accordance with the present invention, when intranasally administered, are effective to cause a peak blood plasma melatonin concentration, or $t_{max}$ within 30 minutes of administration and, preferably, within 15 or 10 minutes of administration.

Preferably, compositions in accordance with this aspect of the invention comprise less than 5–1% by volume of ethanol and less than 20–5% by weight of propylene glycol.

The "blood plasma melatonin concentration" can be a mean value measured in a study of the type described in Example 4 below. Such studies or trials are well known to those skilled in the art.

When used in this specification, the term "single or simultaneous intranasal administration" encompasses both the administration of a single dose or dose form, such as a single insulation of a powder, or a single application of a spray, and the contemporaneous administration of a plurality of such doses or dose forms, (for example, the administration of two squirts of a spray or powder insufflations, one in each nostril).

It has also been found that glycerol and cyclodextrin, when employed in nasal compositions containing melatonin, do not exhibit the unwanted toxic and adverse effects previously noted with the use of (poly)alcohols. It has further been found that cyclodextrin accelerates the absorption of melatonin in the nasal mucosa.

Thus, in a second aspect, the present invention provides a pharmaceutical composition for intranasal administration, comprising melatonin and an additive, wherein the additive comprises cyclodextrin or glycerol. Such pharmaceutical compositions can be in accordance with the first aspect of the invention and can be in the form of an aqueous or a powdered composition. When the composition is aqueous, the additive can be a cyclodextrin, optionally in admixture with glycerol. When the composition is powdered, the additive is preferably a cyclodextrin. The preferred cyclodextrin is β-cyclodextrin. Such compositions are pharmaceutically acceptable because they do not cause the serious local irritation, pain and toxic side effects caused by the (poly)alcohols used in previously proposed compositions.

Nasal compositions in accordance with the invention can be administered as a nasal spray, drop, solution, suspension, gel, ointment, cream, or powder. The composition may also be administered using a nasal tampon or a nasal sponge. As previously stated, the composition is preferably administered in the form of an aqueous composition or a dry powder. The aqueous composition is preferably an aqueous solution, but can be a suspension, or a gel.

When taken as an aqueous composition suitable compositions can be obtained with or without glycerol as an additive. Glycerol allows aqueous compositions containing relatively high amounts of melatonin, does not exert toxicity towards the epithelial membrane, and does not lead to irritation of the nasal mucosa. An additional advantage of the use of glycerol is the preservative properties thereof, leading to stable solutions.

When taken as a powder, the composition preferably contains cyclodextrin and more preferably a melatonin-cyclodextrin complex to obtain optimum onset times.

Melatonin-cyclodextrin complexes, however, can be employed in any embodiment of the present invention.

The term cyclodextrin refers to cyclodextrins such as α-cyclodextrin, β-cyclodextrin, γ-cyclodextrin, and derivatives thereof, such as methylated or alkylated cyclodextrins. Examples are methylated β-cyclodextrin, hydroxypropyl- and hydroxyethyl-cyclodextrin (di)glucosyl- or (di) maltosyl-cyclodextrins carboxymethyl- or sulfoalkylether cyclodextrins, such as sulfobutylether-β-cyclodextrin. The preferred cyclodextrin is methylated β-cyclodextrin, or more preferred β-cyclodextrin.

When a complex of melatonin and cyclodextrin is used, and additionally glycerol is used as a further additive, the ratio of glycerol:cyclodextrin may vary between 1:5 and 500:1 by weight, and preferably between 1:1 and 50:1 by weight.

Pharmaceutical compositions in accordance with the present invention can be formulated to provide a single melatonin dose of between 10 µg and 1 mg and, preferably, of between 0.8, 0.6, 0.5 or 0.4 mg and 0.2, 0.15, 0.1 or 0.05 mg. When used in such low doses, compositions in accordance with the invention will still provide a sufficiently high peak melatonin blood plasma concentration ($t_{max}$) sufficiently soon after administration to be effective in the treatment of human disease, particularly insomnia, or in causing drowsiness or sleep in humans. Thus, the present invention allows effective melatonin blood plasma concentrations to be achieved even when using extremely low melatonin doses.

In preferred embodiments, pharmaceutical compositions in accordance with the invention comprise aqueous compositions of 0.1 to 10 mg/ml of melatonin, and one or more of 1 to 250 mg/ml of cyclodextrin and 5 to 50% by volume of glycerol, or powdered compositions of 0.5 to 50% by weight of melatonin, and 2.5 to 90% by weight of a cyclodextrin. Such a nasal powder can comprise daily doses or dosage units of 0.01 to 1 mg of melatonin, and preferably of about 0.1 to 0.8 mg of melatonin, for sleep induction in man.

In a third aspect, the present invention provides a pharmaceutical dose or dose form comprising sufficient of a pharmaceutical composition in accordance with the first or second aspect of the invention to contain up to 1 mg, 0.8 mg, 0.6 mg, 0.5 mg or 0.4 mg of melatonin and, preferably, at least 0.01 mg, 0.05 mg, 0.1 mg, 0.15 mg or 0.2 mg of melatonin. Said pharmaceutical dose can be in any of the aforementioned forms, including a measured quantity of a liquid for application as a spray or in drops, a spray or drop of liquid, or a powder.

A pharmaceutical dose or dose unit in accordance with the invention preferably contains an additive selected from glycerol, cyclodextrin, and mixtures thereof, and will give effective sleep-induction in man.

In a further aspect, the present invention provides a pharmaceutical product, comprising apparatus for intranasally administering a pharmaceutical dose or dose form in accordance with the third aspect of the invention, and a pharmaceutical composition in accordance with the first or second aspect of the invention. The apparatus can comprise a reservoir and means for expelling the pharmaceutical dose in the form of a spray, wherein a quantity of the pharmaceutical composition is contained within the reservoir. In an embodiment, the apparatus comprises a pump spray device in which the means for expelling a dose comprises a metering pump. In an alternative embodiment, the apparatus comprises a pressurized spray device, in which the means for expelling a dose comprises a metering valve and the pharmaceutical composition further comprises a conventional propellant. Suitable propellants include one or mixture of chlorofluorocarbons, such as dichlorodifluoromethane, and the more recent and preferred hydrofluorocarbons, such as 1,1,1,2-tetrafluoroethane (HFC-134a) and 1,1,1,2,3,3,3 -heptafluoropropane (HFC-227). Suitable pressurized spray devices are well known in the art and include those disclosed in, inter alia, WO92/11190, U.S. Pat. No. 4,819,834, U.S. Pat. No. 4,407,481 and WO97/09034, when adapted for producing a nasal spray, rather than an aerosol for inhalation, or a sublingual spray. Suitable nasal pump spray devices include the VP50, VP70 and VP100 models available from Valois S.A. in Marly Le Roi, France and the 50, 70 and 100 µl nasal pump sprays available from Pfeiffer GmbH in Radolfzell, Germany, although other models and sizes can be employed. In the aforementioned embodiments, a pharmaceutical dose or dose unit in accordance with the invention can be present within the metering chamber of the metering pump or valve.

Pharmaceutical compositions, doses or products in accordance with the present invention are useful in the treatment of human diseases known to be responsive to melatonin, including insomnia, and for inducing drowsiness or sleep in human subjects. They also provide a fast onset time and are suitable for intranasal use. Although not wishing to be bound by any particular theory, it is considered that the capacity of compositions in accordance with the present invention for providing high blood plasma melatonin concentrations very rapidly after administration, on the basis of significantly reduced doses of melatonin, leads to their enhanced efficacy and reduces the likelihood of any unwanted side-effects being caused.

In a yet further aspect of the present invention, there is provided the use of melatonin for the preparation of a pharmaceutical composition, dose or product in accordance with any previously described aspect of the invention, for treating insomnia, or inducing sleep or drowsiness. Use of a pharmaceutical composition, dose or product in accordance with any previous aspect of the invention, for the preparation of a medicament for treating insomnia, or inducing sleep or drowsiness, is also encompassed by the present invention.

The invention also comprises methods for treating disease, including insomnia, and for inducing sleep in humans by intranasally administering a pharmaceutical composition in accordance with the first or second aspect of the invention or a pharmaceutical dose in accordance with the third aspect of the invention. The preferred unit dose is 0.01 to 1 mg of melatonin, and more preferably is 0.1 to 0.8 mg of melatonin.

Pharmaceutically suitable auxiliaries and liquids, such as those described in the standard reference, Gennaro et al., Remington's Pharmaceutical Sciences, (18th ed., Mack Publishing Company, 1990, see especially Part 8: Pharmaceutical Preparations and Their Manufacture) can be included in compositions of the present invention. Such compositions can be processed into vials or containers, for instance, to provide a spray as aforesaid. For making dose units, any pharmaceutically acceptable additives or excipients which do not interfere with the function of the active compound can be used.

To further improve the absorption of melatonin from the nasal composition, nasal absorption enhancers, which are known in the art, may be added. Also viscosity enhancers may be added, for example natural gums, cellulose derivatives such as hydroxypropylmethyl cellulose or methyl cellulose, acrylic polymers (carbopol), and vinyl polymers (polyvinylpyrrolidone). Other conventional pharmaceutically acceptable excipients may also be added, such as preservatives, surfactants, colorants, co-solvents, adhesives, anti-oxidants, buffers, and agents to adjust the pH and cosmolarity.

Nasal powder compositions can be made by mixing the active ingredients and the excipients, both possessing the desired particle size. Other methods to make a suitable powder formulation are the preparation of a solution of active ingredients and excipients, followed by precipitation, filtration, and pulverization, or followed by removal of the solvent by freeze-drying, followed by pulverization of the powder to the desired particle size. The final step can be sieving to obtain particles with a size of less than 100 μm in diameter, preferably between 50 and 100 μm in diameter. Powders can be administered using a nasal insufflator, a jet-spray, or any other conventional device known in the art.

The invention is further illustrated by the following examples.

EXAMPLE 1

A solution was prepared from the following ingredients:

| melatonin | 50 mg |
| 1:1 molar complex of melatonin and β-cyclodextrin | 900 mg |
| sodium chloride | 900 mg |
| benzalkonium chloride | 10 mg |
| sodium EDTA | 100 mg |
| sterilized water | up to 100 ml |

The solution was filtered, stored at 5° C. for 24 h, and filtered again. The solution was then packaged into vials or pump spray devices, each containing 10 ml of the solution and arranged to provide 100 doses of 0.2 mg of melatonin.

EXAMPLE 2

In a reaction vessel, 200 mg of melatonin and 900 mg of sodium chloride were agitated at room temperature in a mixture of 30 ml of glycerol and sufficient water to make the total volume up to 100 ml, until a clear solution was obtained. The solution was filtered, stored at 5° C. for 24 h, and filtered again. This solution can be packaged into vials or containers as discussed in Example 1 and each 10 ml aliquot can provide 100 dose units of 0.2 mg melatonin.

EXAMPLE 3

A solution was prepared containing 200 mg of melatonin., 1.2 g of a complex of 200 mg of melatonin and 1 g of β-cyclodextrin, 5 g of sorbitol, 10 ml of glycerol, and 10 mg of benzalkonium chloride in sufficient water to make the total volume up to 100 ml. The solution was filtered, stored at 5° C. for 24 h, and filtered again. This solution can be packaged into vials or containers as discussed in Example I and, for instance, a container filled with 10 ml of the solution will contain 100 doses of 0.4 mg of melatonin.

EXAMPLE 4

An open randomized, four treatment (treatments A, B, C and D below), cross-over study involving 8 healthy male volunteers was carried out. Before drug administration, the subjects were fasted overnight for at least 10 hours. The administered formulations were as follows:

A: 100 μl water, intranasal (placebo);

B: 200 μg of melatonin in a 100 μl dose of an aqueous solution prepared by the method of Example 1, administered intranasally to one nostril;

C: 400 μg of melatonin in two 100 μl doses of an aqueous solution prepared by the method of Example 1, each administered intranasally to a separate nostril;

D: 2.5 mg of melatonin in an immediate release oral tablet taken with 100 ml of water.

After administration, blood plasma melatonin concentrations were measured in the volunteers by radioimmunoassay and the results are set out in Tables 1, 2 and 3.

BRIEF DESCRIPTION OF THE DRAWING

The results set out in Table 1 are also illustrated graphically in FIG. 1 in which MLT stands for melatonin and N is the number of volunteers in the study.

It was noted that all treatments, both nasal and oral, were safe and well tolerated with no adverse events being reported.

These results show that nasally administered melatonin was absorbed extremely rapidly and that peak plasma concentrations ($C_{max}$) were proportional for the 0.2 and 0.4 mg nasal doses and took place at a $t_{max}$ of less than 10 minutes after administration, compared to a $t_{max}$ of 1.5 hours for the orally administered 2.5 mg melatonin tablets (see Table 2).

About the same amount of melatonin was absorbed from the 0.2 mg nasal dose as was absorbed from the 2.5 mg oral dose and the amount of melatonin absorbed from the 0.4 mg nasal dose was found to be proportional to that absorbed from the 0.2 mg nasal dose.

Although the 0.2 and 0.4 mg nasal doses were much lower than the 2.5 mg oral dose, they produced peak plasma concentrations ($C_{max}$) which were about 5 and 11 times, respectively, higher than that resulting from the oral dose (see Table 3).

The peak melatonin plasma concentrations noted were unexpectedly high and achieved in a surprisingly short period of time. These properties mean that compositions in accordance with the present invention are surprisingly effective and useful in treating insomnia, or causing drowsiness or sleep, when compared to previously known oral compositions. The high peak levels provide an enhanced effect and the rapid onset means that compositions in accordance with the present invention can be taken immediately before their effect is required, rather than 1–2 hours beforehand. Moreover, the total dose required to provide a useful effect is much lower than previously required. Accordingly, compositions in accordance with the present invention are not only more effective than previously proposed oral compositions, but they can achieve their effect at lower dose levels than those previously proposed.

TABLE 1

Plasma melatonin concentrations (mean ± SD).

| TIME AFTER DOSING | TREATMENT A [pg/ml] | TREATMENT B [pg/ml] | TREATMENT C [pg/ml] | TREATMENT D [pg/ml] |
|---|---|---|---|---|
| 0 hours | 12.6 ± 8.31 | 14.1 ± 8.23 | 17.9 ± 5.37 | 16.1 ± 4.00 |
| 5 min | 12.6 ± 8.63 | 5399 ± 1154 | 11436 ± 3150 | 37.0 ± 20.1 |
| 10 min | 12.3 ± 8.10 | 3747 ± 906 | 7515 ± 1944 | 130 ± 103 |
| 15 min | 12.1 ± 7.91 | 2537 ± 628 | 5293 ± 2149 | 277 ± 281 |
| 20 min | 11.6 ± 7.60 | 1916 ± 472 | 3912 ± 1465 | 403 ± 540 |
| 40 min | 13.8 ± 10.7 | 1037 ± 437 | 2259 ± 783 | 906 ± 1346 |
| 1 hours | 11.6 ± 7.61 | 637 ± 369 | 1460 ± 601 | 1266 ± 1741 |
| 1.5 hours | 13.5 ± 6.93 | 455 ± 265 | 941 ± 508 | 1523 ± 1768 |
| 2 hours | 12.0 ± 8.25 | 332 ± 236 | 574 ± 429 | 1438 ± 1318 |
| 2.5 hours | 11.8 ± 7.94 | 238 ± 225 | 418 ± 397 | 981 ± 874 |
| 3 hours | 15.3 ± 7.61 | 156 ± 117 | 293 ± 246 | 629 ± 485 |
| 4 hours | 13.1 ± 5.69 | 101 ± 78.4 | 153 ± 106 | 230 ± 157 |
| 5 hours | 12.0 ± 8.29 | 43.1 ± 32.4 | 70.6 ± 45.5 | 101 ± 108 |
| 6 hours | 11.7 ± 8.03 | 29.7 ± 13.4 | 43.4 ± 19.9 | 60.3 ± 64.8 |
| 8 hours | 12.9 ± 8.62 | 23.6 ± 6.68 | 31.2 ± 9.06 | 37.5 ± 18.8 |

TABLE 2

PHARMACOKINETICS
Pharmacokinetic parameters after single-dose administration of treatments A, B, C and D (mean ± SD)

| PARAMETERS | | TREATMENT A | TREATMENT B | TREATMENT C | TREATMENT D |
|---|---|---|---|---|---|
| AUC | pg · h/ml | 115 ± 49.6 | 2796 ± 1000 | 5725 ± 2015 | 3852 ± 3727 |
| $C_{max}$ | pg/ml | 18.5 ± 7.8 | 5169 ± 1305 | 11437 ± 3151 | 1790 ± 1798 |
| $t_{max}$ | h | 2.66 ± 2.54 | 0.10 ± 0.04 | 0.08 ± 0.00 | 1.56 ± 0.42 |
| t½ | h | | 1.04 ± 0.30 | 1.00 ± 0.20 | 0.90 ± 0.24 |

AUC: Area under the plasma concentration – time curve
$C_{max}$: peak plasma concentration (average value using "best fit" curve)
$t_{max}$: time to reach to $C_{max}$
t1/2: half-life of elimination

TABLE 3

RATIO ESTIMATES AND 90%-CONFIDENCE INTERVALS

| COMPARISON | PARAMETER | N | RATIO ESTIMATE | 90% CI |
|---|---|---|---|---|
| C to B | AUC | 8 | 2.03 | 1.10–3.76 |
| | $C_{max}$ | 8 | 2.20 | 1.20–4.04 |
| C to D | AUC | 8 | 2.34 | 1.26–4.33 |
| | $C_{max}$ | 8 | 11.0 | 6.01–20.3 |
| B to D | AUC | 8 | 1.15 | 0.62–2.13 |
| | $C_{max}$ | 8 | 5.02 | 2.73–9.23 |

N = number of volunteers in the survey.

I claim:

1. A pharmaceutical composition for intranasal administration, comprising melatonin and a pharmaceutically acceptable excipient, said composition being effective to cause the blood plasma melatonin concentration in a human adult, receiving an amount of melatonin in the range of 50–1000 µg and in a single or simultaneous intranasal administration of said composition, to reach at least X pg/ml, within 30 minutes of said administration, wherein X is equal to 5 times the amount of melatonin, expressed in µg, in said single or simultaneous administration.

2. The pharmaceutical composition of claim 1, wherein X is equal to 10 times the amount of melatonin, expressed in µg, in said single or simultaneous administration.

3. The pharmaceutical composition of claim 1, wherein X is equal to 15 times the amount of melatonin, expressed in µg, in said single or simultaneous administration.

4. The pharmaceutical composition of claim 1, wherein X is equal to 20 times the amount of melatonin, expressed in µg, in said single or simultaneous administration.

5. The pharmaceutical composition of claim 1, wherein X is equal to 25 times the amount of melatonin, expressed in µg, in said single or simultaneous administration.

6. The pharmaceutical composition of claim 1, effective to cause the blood plasma melatonin concentration in a human adult, receiving 200 µg of melatonin in a single or simultaneous intranasal administration of said composition, to reach at least 1000 pg/ml within 30 minutes of administration.

7. The pharmaceutical composition of claim 6, wherein the melatonin concentration reaches at least 2000 pg/ml within 30 minutes after intranasal administration.

8. The pharmaceutical composition of claim 6, wherein the melatonin concentration reaches at least 3000 pg/ml within 30 minutes after intranasal administration.

9. The pharmaceutical composition of claim 6, wherein the melatonin concentration reaches at least 4000 pg/ml within 30 minutes after intranasal administration.

10. The pharmaceutical composition of claim 6, wherein the melatonin concentration reaches at least 5000 pg/ml within 30 minutes after intranasal administration.

11. The pharmaceutical composition of claim 1, wherein said melatonin concentration is reached within 15 minutes or less after intranasal administration.

12. The pharmaceutical composition of claim 11, wherein said melatonin concentration is reached within 10 minutes or less after intranasal administration.

13. The pharmaceutical composition of claim 11, wherein said melatonin concentration is reached within 8 minutes or less after intranasal administration.

14. The pharmaceutical composition of claim 11, wherein said melatonin concentration is reached within 7 minutes or less after intranasal administration.

15. The pharmaceutical composition of claim 11, wherein said melatonin concentration is reached within 6 minutes or less after intranasal administration.

16. The pharmaceutical composition of claim 11, wherein said melatonin concentration is reached within 5 minutes or less after intranasal administration.

17. The pharmaceutical composition of claim 1, further comprising an additive selected from the group consisting of a cyclodextrin, glycerol, and admixtures thereof.

18. A pharmaceutical composition for intranasal administration comprising melatonin and an additive selected from the group consisting of a cyclodextrin, glycerol, and admixtures thereof.

19. The pharmaceutical composition of claim 18, in the form of an aqueous or a powdered composition.

20. The pharmaceutical composition of claim 18, wherein the additive is selected from the group consisting of a cyclodextrin and an admixture of a cyclodextrin with glycerol, and the composition is aqueous.

21. The pharmaceutical composition of claim 18, wherein the additive is a cyclodextrin and the composition is powdered.

22. The pharmaceutical composition of claim 18, wherein said cyclodextrin is β-cyclodextrin.

23. The pharmaceutical composition of claim 18, comprising an aqueous solution of 0.1–10 mg/ml of melatonin.

24. The pharmaceutical composition of claim 23 further comprising 1–250 mg/ml of a cyclodextrin.

25. The pharmaceutical composition of claim 23 further comprising 5–50 percent by volume of glycerol.

26. The pharmaceutical composition of claim 18 comprising a complex of melatonin and cyclodextrin.

27. The pharmaceutical composition of claims 1 or 18, comprising an aqueous medium and less than 5% by volume of ethanol.

28. The pharmaceutical composition of claims 1 or 18 comprising an aqueous medium and less than 4% by volume of ethanol.

29. The pharmaceutical composition of claims 1 or 18 comprising an aqueous medium of less than 3% by volume of ethanol.

30. The pharmaceutical composition of claims 1 or 18 comprising an aqueous medium of less than 2% by volume of ethanol.

31. The pharmaceutical composition of claims 1 or 18 comprising an aqueous medium of less than 1% by volume of ethanol.

32. The pharmaceutical composition of claims 1 or 18, comprising an aqueous medium and less than 20 percent by weight of propylene glycol.

33. The pharmaceutical composition of claims 1 or 18 comprising an aqueous medium and less than 15% by weight of propylene glycol.

34. The pharmaceutical composition of claims 1 or 18 comprising an aqueous medium and less than 10% by weight of propylene glycol.

35. The pharmaceutical composition of claims 1 or 18 comprising an aqueous medium and less than 5% by weight of propylene glycol.

36. The pharmaceutical composition of claims 1 or 18, characterized by being formulated to provide a single dose of melatonin of between 10 $\mu$g and 1 mg.

37. A pharmaceutical dose comprising sufficient of the pharmaceutical composition of claims 1 or 18 to contain 10 $\mu$g–1 mg of melatonin.

38. A pharmaceutical product comprising an apparatus for intranasally administering a pharmaceutical dose containing between 0.01–1 mg of melatonin of the pharmaceutical composition of claims 1 or 18.

39. The pharmaceutical product of claim 38, wherein the apparatus comprises a reservoir and means for expelling the pharmaceutical dose in the form of a spray, wherein a quantity of the pharmaceutical composition is contained within the reservoir.

40. The pharmaceutical product of claim 39, comprising a pump spray device, wherein the means for expelling a dose comprises a metering pump.

41. The pharmaceutical product of claim 39, comprising a pressurized spray device, wherein the means for expelling a dose comprises a metering valve and the pharmaceutical composition further comprises a propellant.

42. A method of treating a human in need of melatonin therapy comprising the intranasal administration to a human of an effective amount of a pharmaceutical composition suitable for intranasal use and comprising melatonin and a pharmaceutically acceptable excipient, wherein said composition is effective to cause the blood plasma melatonin concentration in a human adult, receiving an amount of melatonin in the range 50–1000 $\mu$g and in a single or simultaneous intranasal administration of said composition, to reach at least X pg/ml, within 30 minutes of said administration, wherein X is equal to 5 times the quantity of melatonin, expressed in $\mu$g, in said single or simultaneous administration.

43. The method of claim 42, wherein X is equal to 10 times the amount of melatonin, expressed in $\mu$g, in said single or simultaneous administration.

44. The method of claim 42, wherein X is equal to 15 times the amount of melatonin, expressed in $\mu$g, in said single or simultaneous administration.

45. The method of claim 42, wherein X is equal to 20 times the amount of melatonin, expressed in $\mu$g, in said single or simultaneous administration.

46. The method of claim 42, wherein X is equal to 25 times the amount of melatonin, expressed in $\mu$g, in said single or simultaneous administration.

47. The method of claim 42, wherein said pharmaceutical composition is effective to cause the blood plasma melatonin concentration in a human adult, receiving 200 $\mu$g of melatonin in a single or simultaneous intranasal administration of said composition, to reach at least 1000 pg/ml within 30 minutes of administration.

48. The method of claim 47, wherein the melatonin concentration reaches at least 2000 pg/ml within 30 minutes of administration.

49. The method of claim 47, wherein the melatonin concentration reaches at least 3000 pg/ml within 30 minutes of administration.

50. The method of claim 47, wherein the melatonin concentration reaches at least 4000 pg/ml within 30 minutes of administration.

51. The method of claim 47, wherein the melatonin concentration reaches at least 5000 pg/ml within 30 minutes of administration.

52. The method of claim 42, wherein said melatonin concentration is reached within 5–15 minutes of administration.

53. The method of claim 42, wherein the pharmaceutical composition comprises melatonin and an additive.

54. A method of treating a human in need of melatonin therapy comprising the intranasal administration to a human of an effective amount of a pharmaceutical composition suitable for intranasal use and comprising melatonin and an additive selected from the group consisting of a cyclodextrin, glycerol, and admixtures thereof.

55. The method of claims 42 or 54, wherein the composition is an aqueous or a powdered composition.

56. The method of claims 42 or 54, wherein the additive is selected from the group consisting of a cyclodextrin, and an admixture of a cyclodextrin with glycerol, and the composition is aqueous.

57. The method of claims 42 or 54, wherein the additive is a cyclodextrin and the composition is powdered.

58. The method of claims 42 or 54, wherein the cyclodextrin is β-cyclodextrin.

59. The method of claims 42 or 54, wherein the composition comprises an aqueous solution of 0.1–10 mg/ml of melatonin.

60. The method of claim 59 wherein the composition further comprises 1–250 mg/ml of a cyclodextrin.

61. The method of claim 59 wherein the composition further comprises 5–50% by volume of glycerol.

62. The method of claim 54, wherein the composition comprises a complex of melatonin and cyclodextrin.

63. The method of claim 54, wherein the composition comprises an aqueous medium and less than 5% by volume of ethanol.

64. The method of claim 54, wherein the composition comprises an aqueous medium and less than 20% by weight of propylene glycol.

65. The method of claim 54, wherein a single or simultaneous dose of between 10 μg and 1 mg of melatonin is administered to said human.

66. A method of inducing drowsiness or sleep in a human, comprising the intranasal administration to a human of an effective amount of a pharmaceutical composition suitable for intranasal use and comprising melatonin and a pharmaceutically acceptable excipient, wherein said composition is effective to cause the blood plasma melatonin concentration in a human adult, receiving an amount of melatonin in the range 50–1000 μg and in a single or simultaneous intranasal administration of said composition, to reach at least X pg/ml, within 30 minutes of said administration, wherein X is equal to 5 times the quantity of melatonin, expressed in μg, in said single or simultaneous administration.

67. The method of claim 66, wherein X is equal to 10 times the amount of melatonin, expressed in μg, in said single or simultaneous administration.

68. The method of claim 66, wherein X is equal to 15 times the amount of melatonin, expressed in μg, in said single or simultaneous administration.

69. The method of claim 66, wherein X is equal to 20 times the amount of melatonin, expressed in μg, in said single or simultaneous administration.

70. The method of claim 66, wherein X is equal to 25 times the amount of melatonin, expressed in μg, in said single or simultaneous administration.

71. The method of claim 66, wherein said pharmaceutical composition is effective to cause the blood plasma melatonin concentration in a human adult, receiving 200 μg of melatonin in a single or simultaneous intranasal administration of said composition, to reach at least 1000 pg/ml within 30 minutes of administration.

72. The method of claim 66, wherein the melatonin concentration reaches at least 2000 pg/ml within 30 minutes of administration.

73. The method of claim 66, wherein the melatonin concentration reaches at least 3000 pg/ml within 30 minutes of administration.

74. The method of claim 66, wherein the melatonin concentration reaches at least 4000 pg/ml within 30 minutes of administration.

75. The method of claim 66, wherein the melatonin concentration reaches at least 5000 pg/ml within 30 minutes of administration.

76. The method of claim 66, wherein said melatonin concentration is reached within 5–15 minutes of administration.

77. The method of claim 66, wherein the pharmaceutical composition comprises melatonin and an additive.

78. A method of inducing drowsiness or sleep in a human, comprising the intranasal administration to a human of an effective amount of a pharmaceutical composition suitable for intranasal use and comprising melatonin and an additive selected from the group consisting of a cyclodextrin, glycerol, and admixtures thereof.

79. The method of claims 66 or 78, wherein the composition is an aqueous or a powdered composition.

80. The method of claims 66 or 78, wherein the additive is selected from the group consisting of a cyclodextrin, and an admixture of a cyclodextrin with glycerol, and the composition is aqueous.

81. The method of claims 66 or 78, wherein the additive is a cyclodextrin and the composition is powdered.

82. The method of claims 66 or 78, wherein the cyclodextrin is β-cyclodextrin.

83. The method of claims 66 or 78, wherein the composition comprises an aqueous solution of 0.1–10 mg/ml of melatonin.

84. The method of claim 83 wherein the composition further comprises 1–250 mg/ml of a cyclodextrin.

85. The method of claim 83 wherein the composition further comprises 5–50% by volume of glycerol.

86. The method of claim 78, wherein the composition comprises a complex of melatonin and cyclodextrin.

87. The method of claim 78, wherein the composition comprises an aqueous medium and less than 5% by volume of ethanol.

88. The method of claim 78, wherein the composition comprises an aqueous medium and less than 20% by weight of propylene glycol.

89. The method of claim 78, wherein a single or simultaneous dose of between 10 μg and 1 mg of melatonin is administered to said human.

90. The pharmaceutical composition of claims 1 or 18, characterized by being formulated to provide a single dose of melatonin of no more than about 1 mg.

91. A pharmaceutical dose comprising sufficient of the pharmaceutical composition of claims 1 or 18 to contain melatonin in an amount of no more than about 1 mg.

92. A pharmaceutical product comprising an apparatus for intranasally administering the pharmaceutical composition of claims 1 or 18 to provide a dose of melatonin in an amount of no more than about 1 mg.

93. The method of claim 54, wherein a single or simultaneous dose of melatonin is administered in an amount of no more than about 1 mg.

94. The method of claim 78, wherein a single or simultaneous dose of melatonin is administered in an amount of no more than about 1 mg.

* * * * *